US00RE42606E

(19) United States
(12) Reissued Patent
Bell et al.

(10) Patent Number: US RE42,606 E
(45) Date of Reissued Patent: Aug. 16, 2011

(54) LOW INSERTION FORCE TIP/MANDREL

(75) Inventors: David W. Bell, Anaheim, CA (US); Westley D. Peters, Chino Hills, CA (US)

(73) Assignee: Beckman Coulter, Inc., Brea, CA (US)

(21) Appl. No.: 12/001,750

(22) Filed: Dec. 11, 2007

Related U.S. Patent Documents

Reissue of:
(64) Patent No.: 6,973,845
Issued: Dec. 13, 2005
Appl. No.: 09/764,691
Filed: Jan. 18, 2001

(51) Int. Cl.
*G01N 1/00* (2006.01)
(52) U.S. Cl. ..... 73/864.14
(58) Field of Classification Search ..... None
See application file for complete search history.

(56) References Cited

U.S. PATENT DOCUMENTS

| | | | | |
|---|---|---|---|---|
| 2,946,486 | A | 7/1960 | Gilmont | 222/38 |
| 4,084,730 | A | 4/1978 | Franke et al. | 222/309 |
| 4,099,548 | A | 7/1978 | Sturm et al. | 141/27 |
| 4,257,267 | A | 3/1981 | Parsons | 73/425.6 |
| 4,362,064 | A | 12/1982 | Marteau d'Autry | 73/864.13 |
| 4,369,665 | A | 1/1983 | Citrin | 73/864.18 |
| 4,418,580 | A | 12/1983 | Satchell et al. | 73/864.13 |
| 4,435,989 | A | 3/1984 | Meyer et al. | 73/864.14 |
| 4,567,780 | A | 2/1986 | Oppenlander et al. | 73/864.16 |
| 4,616,514 | A | 10/1986 | Magnussen, Jr. et al. | 73/864.14 |
| 4,748,859 | A | 6/1988 | Magnussen, Jr. et al. | 73/864.01 |
| 4,779,467 | A | 10/1988 | Rainin et al. | 73/864.17 |
| 4,824,641 | A * | 4/1989 | Williams | 422/100 |
| 4,863,695 | A | 9/1989 | Fullemann | 422/100 |
| 4,961,350 | A | 10/1990 | Tennstedt | 73/864.01 |
| 4,965,050 | A | 10/1990 | Jessop | 422/100 |
| 4,999,164 | A | 3/1991 | Puchinger et al. | 422/100 |
| 5,032,343 | A | 7/1991 | Jeffs et al. | 264/320 |
| 5,063,790 | A | 11/1991 | Freeman et al. | 73/864.14 |
| 5,104,621 | A | 4/1992 | Pfost et al. | 422/67 |
| 5,108,703 | A | 4/1992 | Pfost et al. | 422/65 |
| 5,200,151 | A * | 4/1993 | Long | 422/100 |
| 5,260,030 | A * | 11/1993 | DeVaughn | 422/100 |
| 5,496,523 | A | 3/1996 | Gazit et al. | 422/100 |
| 5,734,114 | A * | 3/1998 | Itoh | 73/864.14 |
| 6,123,905 | A | 9/2000 | Torti et al. | 422/100 |
| 6,143,252 | A | 11/2000 | Haxo, Jr. et al. | 422/131 |
| 7,033,543 | B1 * | 4/2006 | Panzer et al. | 422/100 |

FOREIGN PATENT DOCUMENTS

WO 00/62933 * 10/2000

* cited by examiner

*Primary Examiner* — Robert R Raevis
(74) *Attorney, Agent, or Firm* — Kilpatrick Townsend & Stockton LLP

(57) ABSTRACT

A pipette assembly for automatic pipetting machines including a stepped mandrel and tip for providing a minimum contact seal between the pipette tip and mandrel. The mandrel includes a first cylindrical portion with a first exterior diameter and a second cylindrical portion with a second exterior diameter. Raised bands on the first and second cylindrical portions contact the interior wall of the pipette tip to form seals. Because only a portion of the mandrel, specifically the seal portions, contacts the pipette tip, lower forces are required to insert the tip onto the mandrel.

33 Claims, 3 Drawing Sheets

LOW INSERTION FORCE TIP/MANDREL

Matter enclosed in heavy brackets [ ] appears in the original patent but forms no part of this reissue specification; matter printed in italics indicates the additions made by reissue.

*This application is a reissue application of U.S. Pat. No. 6,973,845, which was derived from U.S. patent application Ser. No. 09/764,691, filed on Jan. 18, 2001, which is herein incorporated by reference in its entirety for all purposes.*

BACKGROUND

1. Field of the Invention

The present invention relates to an apparatus for handling chemical and biological substances, and more particularly to pipetting systems.

2. Background Information

The use of manual, semiautomatic, or automatic pipette devices for the transfer and dispensing of precise quantities of fluids in analytical systems is well known as is the use of disposable pipette tip members. Disposable tips accommodate the serial use of such pipette devices in the transfer of different fluids without carryover or contamination.

A proper seat between the pipette device and disposable tip is essential. Most pipetting systems require a proper seal to create a vacuum for receiving and dispelling samples. Additionally, many analytical processes require very small sample sizes, for example, in the range of 1 to 250 micro liters. If the seal is not air-tight, the pipette device may not pick up the precise amount of sample that the device was set to receive. Therefore, the pipette device may receive and dispel too much or too little sample which could impact the quantitative or qualitative result of the assay. Also, many samples are very expensive and are wasted by unintended oversampling. This results in premature depletion of the sample and, thus, added cost.

Commercially available pipetting devices use several techniques for picking up and discarding disposable pipette tips. Some companies use specially designed mandrels for engagement with disposable pipette tips. These mandrel ends are generally tapered or cylindrical in shape to accommodate pipette tips. Both tapered and cylindrical mandrel ends provide a good seal with the pipette tip and work well to align the tip with the mandrel. However, large insertion forces are required for insertion of the pipette tip onto the tapered or cylindrical mandrel end.

With the tapered mandrel end, the engaged portion of the pipette tip continues stretching as the pipette tip travels farther up the mandrel end which results in an exponential increase in the insertion force required as the pipette tip travels farther up the mandrel. With the cylindrical mandrel end, the engaged portion of the pipette tip is held in the stretched position as the pipette tip travels farther up the mandrel end which results in a roughly linear increase in the insertion force required as the pipette tip travels farther up the mandrel.

To accommodate the large insertion forces required with cylindrical or tapered mandrel ends for automatic pipetting devices, many systems require high-inertia instrument structures to effectively attach and shuck disposable pipette tips. These high-inertia to instrument structures tend to be large and very expensive. Therefore, it is desirable to have a pipetting device and custom molded tip design that minimizes the force necessary to attach and shuck disposable pipette tips, thereby eliminating the need for massive and expensive high-inertia instrumentation systems.

To minimize the force necessary to attach and shuck disposable pipette tips, one pipetting device uses a substantially cylindrical mandrel in conjunction with custom molded pipette tips that have molded rings which act as seals between the mandrel end and the pipette tips. This prior art pipetting device is shown in FIG. 6. As shown in FIG. 6, the molded rings 10 of the pipette tip 100 engage the mandrel 200 to form seals. During insertion of the mandrel 200 into the tip 100, only a substantially constant insertion force is required because only the molded rings 110 contact the surface of the mandrel during insertion and no additional surfaces contact the mandrel as insertion continues. While these pipette tips work fairly well with the devices for which they were designed, many of the tips are damaged during manufacturing. The single-piece core pin which forms the interior of the pipette tip must be pulled out of the tip during molding. Because the seals are on the interior wall of the pipette tip and extend inwardly toward the center axis of the pipette tip, the core pin must contact and pull upon the seals before it can be removed from the pipette tip during molding. This contact can damage the seals thus reducing the percentage of pipette tips that pass quality control testing and thereby resulting in increased manufacturing cost for the pipette tips. Furthermore, pipette tips with only minor damage may pass quality control testing, but may not be able to secure properly to the mandrel because of the damage caused by the molding process. Since most pipetting systems require a proper seal to create a vacuum for receiving and dispelling sample, the pipette device may not pick up the precise amount of sample that the device was set to receive if the pipette tip is not properly secured to the mandrel. Therefore, the pipette device may receive and dispel too much or too little of the sample which could impact the quantitative or qualitative result of the assay. Expensive samples may be wasted as a result.

Another problem with the pipetting device shown in FIG. 6 results because the seals on the pipette tip are resilient. The resilient seals may improperly twist upon insertion of the mandrel into the pipette tip and prevent proper sealing. For example, if significant friction is encountered by a seal as it contacts the mandrel during insertion, the seal may twist or "roll" against the mandrel instead of sliding upon the mandrel. After such twisting, the seal may be deformed and may not properly seat against the mandrel, thereby preventing a proper seal from forming between the mandrel and the pipette tip.

For the foregoing reasons there is a need for a low insertion force custom tip and mandrel design in which the seals are positioned on the pipettor mandrel. This will reduce the need for large and costly high-inertia instrumentation. In addition, it will reduce manufacturing costs associated with pipette tips with molded rings acting as seals since fewer will be damaged during molding.

SUMMARY

The present invention is directed to an apparatus that satisfies the need for a low insertion force custom pipette tip and pipettor mandrel design in which the seals are positioned on the pipettor mandrel.

The pipette mandrel of the present invention is an elongated hollow metallic structure that includes a lead-in portion with a first cylindrical portion adjacent to the lead-in portion. The first cylindrical portion has a first exterior diameter with a first raised band positioned upon the first exterior diameter.

Additionally, the mandrel may include a second cylindrical portion with a second exterior diameter adjacent to the first cylindrical portion. The second cylindrical portion also includes a second raised band positioned upon the second exterior diameter. Both the first and second raised bands are non-resilient and stationary, being integrated as part of the mandrel.

The pipette tip of the present invention includes a collar portion and an adjacent conical head. The conical head is the receptacle portion for receiving fluids. The collar portion is used to connect the pipette tip to the mandrel. The collar portion has an interior cylindrical wall which is defined by a first step portion having a first interior diameter. When the pipette tip is fully inserted onto the mandrel, the first raised band on the mandrel contacts the first step portion of the pipette tip. The interior cylindrical wall of the pipette tip may also have a second step portion having a second interior diameter that may contact a second raised band on the mandrel when fully inserted. Thus, the first raised band on the cylindrical portion contacts the interior wall of the pipette tip to form the first seal. Additionally, the second raised band on the cylindrical portion may contact the pipette tip to form a second seal. At a minimum, the second band is useful in aligning the pipette tip on the mandrel. Because only the seal portions of the mandrel contact the pipette tip, lower forces are required to insert the pipette tip onto the mandrel and remove the pipette tip from the mandrel. Additionally, placement of the seals on the mandrel as opposed to the pipette tips reduces manufacturing costs associated with pipette tips while adding almost no additional cost to mandrel manufacturing. Furthermore, placement of the non-resilient seals upon the mandrel provide for a consistent and reliable seal between the mandrel and the pipette tips.

These and other features, aspects, and advantages of the present invention will become better understood with reference to the following description and appended claims.

DESCRIPTION

Figure 1:
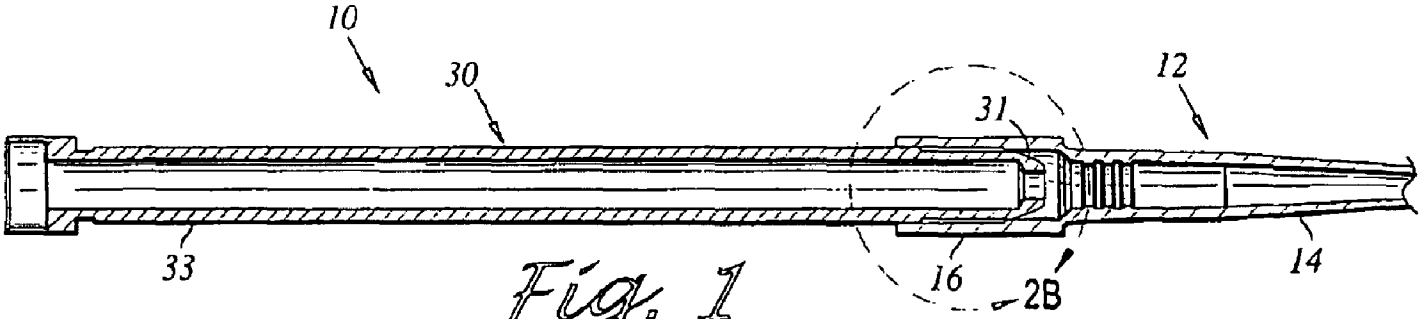
FIG. 1 is a cross-sectional view of a pipettor assembly in accordance with the present invention.
Figure 2A:
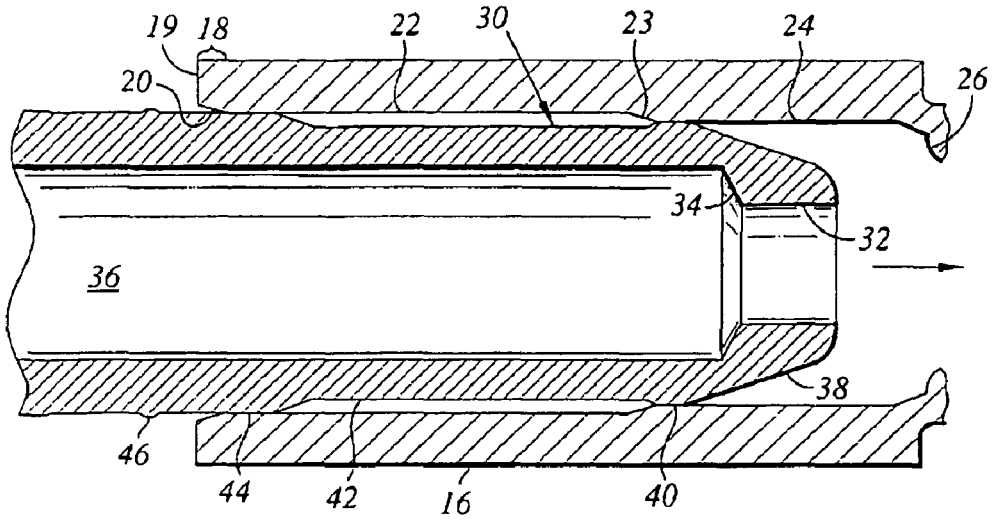
FIG. 2A is an enlarged cross-sectional view of the pipettor assembly showing the portion of the mandrel encircled by line B of FIG. 1.

Referring to FIG. 1, a pipettor assembly 10 in accordance with the present invention includes a pipette tip 12 and a pipettor mandrel 30 having a distal end 31 and a proximate end 33. The pipette tip 12 is generally made from polypropylene, and has an elongated, truncated, body portion with a collar portion 16 and a conical head 14. Referring to FIG. 2A, the collar portion 16 includes a mouth 18 defined by a rim 19 and a funnel-shaped first taper 20. The collar portion 16 further includes a second step 22 which is a cylinder-shaped portion having a substantially constant interior diameter. The second step 22 is defined between the first taper 20 and a second taper 23. The second taper 23 is also funnel-shaped and feeds into a first step 24. Like the second step 22, the first step 24 is also a cylinder-shaped portion having a substantially constant interior diameter. The interior diameter of the first step 24 is smaller than the interior diameter of the second step 22. After the first step 24, the collar portion ends in a positive stop 26. The positive stop is a flange between the collar portion 16 and conical head 14.

The exterior of the mandrel 30 is defined by a tapered lead in 38 on the distal end 31 of the mandrel, followed by a first band 40, a first cylindrical portion 42, a second cylindrical portion 44, and a second band 46. The diameter of the lead in 38 gradually increases from the distal end 31 up to the diameter of the first band 40. The first band 40 is a raised portion on the mandrel 30 adjacent to the lead in 38 upon the first cylindrical portion 42. The first cylindrical portion 42 is an elongated portion of the mandrel 30 extending from the first band 40. The diameter of the first band 40 is slightly larger than the diameter of the first cylindrical portion 42. On the opposite end of the first cylindrical portion 42 from the first band 40, the mandrel 30 tapers into the second cylindrical portion 44, which has a larger diameter than the first cylindrical portion 42. Like the first band 40, the second band 46 is a raised portion upon the mandrel 30. The second band 46 is positioned upon the second cylindrical portion 44 and has a diameter slightly larger than that of the second cylindrical portion 44.

Insertion of the mandrel 30 into the pipette tip 12 is now described with reference first to FIG. 2A. The mouth 18 of the collar portion 16 of the pipette tip 12 is designed to receive the mandrel 30. Upon insertion of the mandrel into the pipette tip, the mandrel lead in 3[$]*8* moves axially towards the positive stop 26 of the pipette tip 12 in the direction of the arrow 31. Initially, the mandrel lead in 38 enters the taper 20 of the pipette tip 12. Next, the first band 40 of the mandrel 30 enters the taper 20 of the pipette tip 12, and then enters the second step 22 of the pipette tip 12. The diameter of the first band 40 is smaller than the diameter of the second step 22 of the pipette tip 12. Thus, as the lead in portion 38, first band 40, and first cylindrical portion 42 enter the second step 22, the first band 40 only occasionally contacts the interior cylindrical walls of the second step 22 of the pipette tip 12. The occasional contacts with the interior cylindrical walls may adjust orientation of the pipette tip 12, causing the pipette tip to properly align with the mandrel 30 during insertion. Additional alignment occurs when the first band 40 of the mandrel 30 moves past the second taper 23 and into the first step 24 of the pipette tip 12. As shown in FIG. 2A, sealing occurs when the first band 40 of the mandrel 30 fully engages the first step 24 of the pipette tip 12 causing a portion of said first step 24 to be displaced because the diameter of the first seal is slightly larger than the diameter of the first step. When the first step 24 is displaced, it presses against the first band 40 to form an air-tight seal between the mandrel and tip. Thus, at this point, the pipette tip 12 will stay on and seal. Sealing continues to occur as the first band 40 moves in the direction of the arrow 31 toward the positive stop 26.

The first cylindrical portion 42 of the mandrel 30 does not generally contact the interior cylindrical wall of the pipette tip 12 as the mandrel is inserted because the diameter of the first cylindrical portion is less than the interior diameter of both the second step 22 and the first step 24 of the pipette tip 12.

However, there may be some incidental contact between the first cylindrical portion 42 and the first step 24, depending upon manufacturing tolerances, but this incidental contact does not contribute any significant resistance during insertion. Because only a portion of the mandrel 30, specifically the first band 40, contacts the pipette tip 12, roughly constant insertion forces are required to insert the mandrel into the tip once the first band fully engages the mandrel. This constant insertion force provides an advantage over other pipettor assemblies where a greater portion of the mandrel contacts the tip.

Figure 2B:
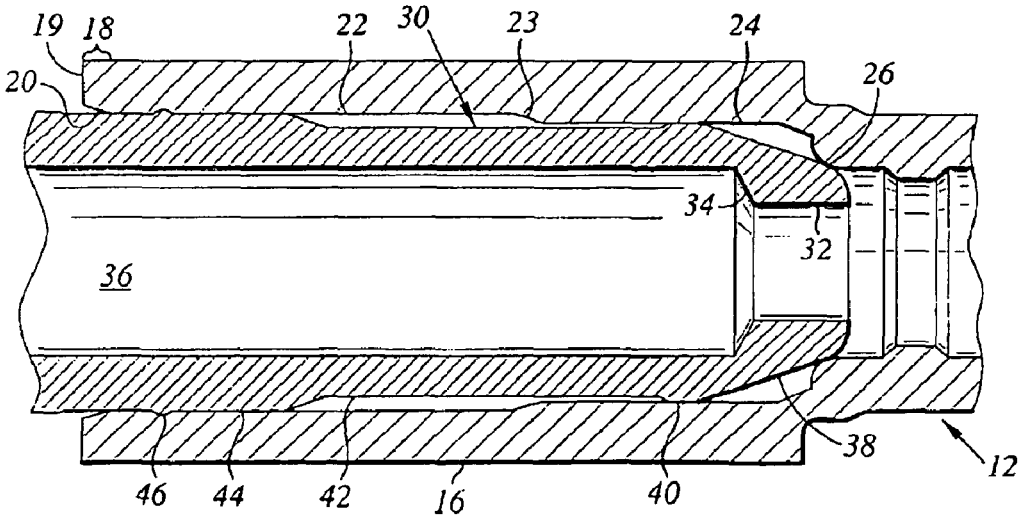
FIG. 2B is another cross-sectional view of the pipettor assembly shown in FIG. 2A with the mandrel more fully inserted into the pipette tip.

Final alignment occurs when the second cylindrical portion 44 and the second band 46 of the mandrel 30 enters the taper 20 and second step 22 of the pipette tip 12. As shown in FIG. 2B, a second seal may be formed, depending upon tolerances, if the second band 46 of the mandrel 30 engages the second step 22 of the pipette tip 12 causing a portion of said 1 second step 22 to stretch. As with the first seal, roughly constant insertion forces are required if a second seal is formed because only the second band 46 contacts the interior wall of the second step 22 of the pipette tip 12. The mandrel 30 is fully inserted into the tip 12 when the mandrel lead in 38 abuts the positive stop 26 on the pipette tip 12.

As with insertion, the forces required to remove the mandrel 30 from the tip 12 are roughly constant during removal. During removal, if a second seal has been formed between the second band 46 and the second step 22 of the pipette tip 12, contact is maintained between the second band 46 and the interior wall of the second step 22 of the pipette tip 12 until the second band clears the second step and enters the first taper portion 20 of the mouth 18 of the pipette tip. The second cylindrical portion 44 of the mandrel 30 does not continually contact the interior wall of the first taper 20 of the pipette tip 12 as the mandrel is removed because the diameter of the first taper of the pipette tip is larger than the diameter of the second cylindrical portion 44. There may be some incidental contact between the second cylindrical portion 44 and the first taper 20, but this incidental contact does not contribute any significant resistance during removal.

The first seal is maintained during removal until the first band 40 clears the first step 24 of the pipette tip 12. The first band 40 then enters the second taper 23 followed by the second step 22 of the pipette tip 12. As the first band 40 is removed from the tip 12, the first band of the mandrel 30 does not generally contact the interior wall of the second step 22 or first taper 20 since the diameters of the second step and first taper are both larger than the diameter of the first band. There may be some incidental contact between the first cylindrical portion 42 and the second step 22 or first taper 20, but this incidental contact does not contribute any significant resistance during insertion. Therefore, removal forces are similar to the roughly constant insertion forces.

Since the seals for the pipettor assembly 10 are on the mandrel and not on the interior wall of the pipette tip, greater manufacturing yields of the pipette tips can be attained. As discussed previously, a core pin which forms the interior of the pipette tip must be pulled out of the tip during manufacturing. When the seals are on the interior wall of the pipette tip as with some prior pipette tips, the core pin must be dragged across the seals in order to remove the core pin from the mold, thus increasing the likelihood of damage to the seals. In contrast, during removal of the core pin from the pipette tips of the present invention, the core pin is 1 pulled out of the pipette through portions of the pipette tip with increasingly greater diameters, thereby eliminating any drag. Thus, fewer pipette tips are damaged during manufacturing when the seals are positioned on the mandrel and not the pipette tip.

Furthermore, since the seals for the pipettor assembly 10 are on the non-resilient mandrel 30 and not on the resilient interior wall of the pipette tip 12, there is no twisting of the seals upon insertion of the tip onto the mandrel. As discussed previously, when the seals are resilient and located on the pipette tip, they may improperly twist upon insertion of the mandrel into the pipette tip and prevent proper sealing. However, the present invention avoids this problem by integrating non-resilient seals onto the mandrel. When such seals are positioned on the mandrel 30 and not the pipette tip 12, twisting of the seals upon insertion of the tip onto the mandrel is eliminated and a proper seal is consistently formed between the mandrel and the pipette tip.

Figure 4:
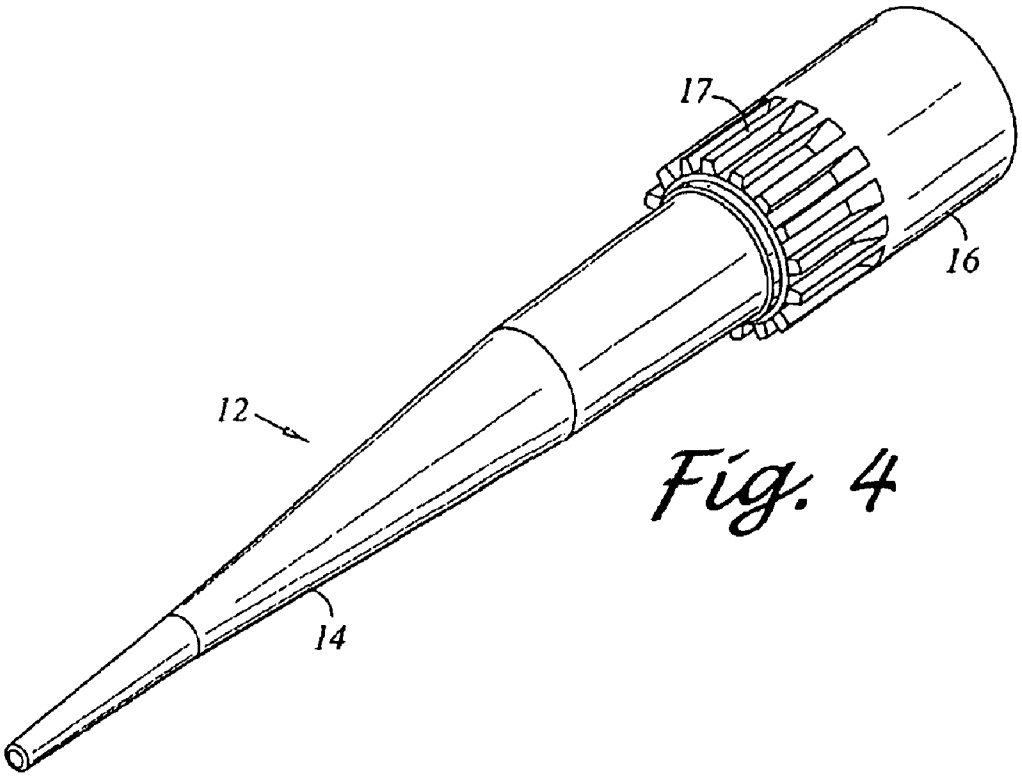
FIG. 4 is a perspective view of the pipette tip which illustrates an alternative embodiment of the invention in which the collar portion of the pipette tip has external ribs.
Figure 3:
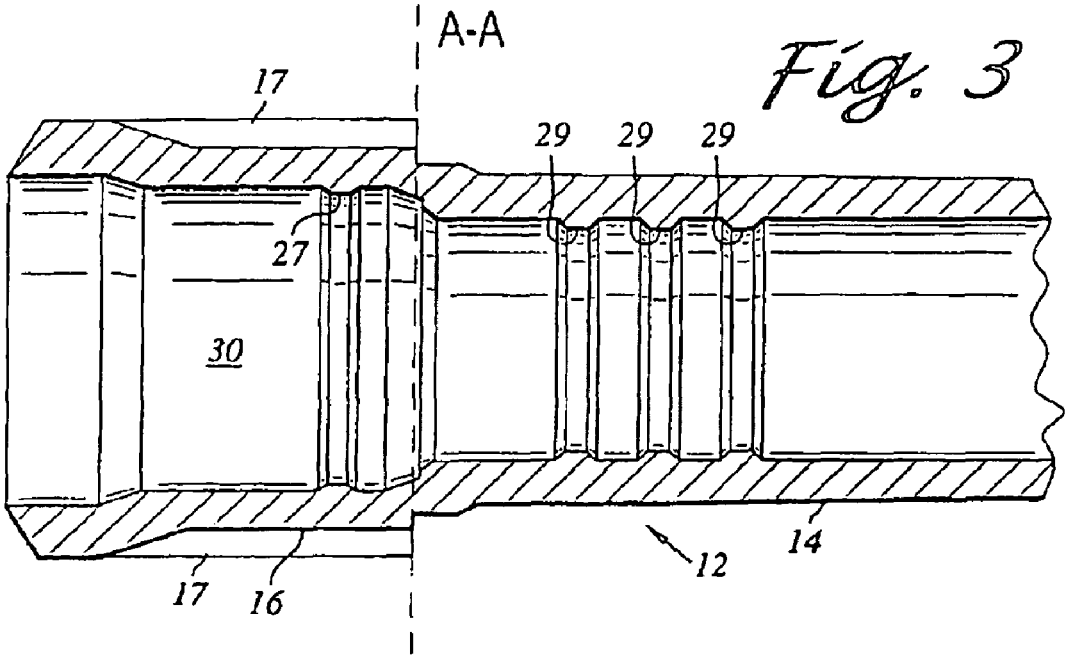
FIG. 3 is a cross-sectional view of the pipettor assembly which illustrates an alternative embodiment of the invention in which an internal molded ring on the pipette tip is the positive stop.
Figure 5:
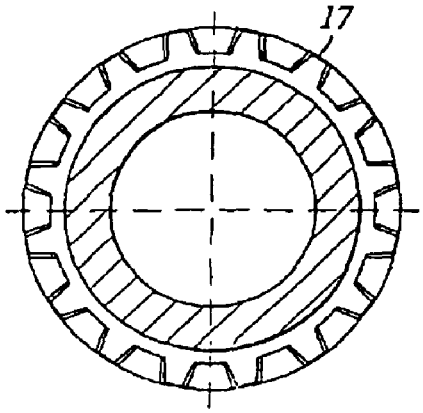
FIG. 5 is a cross sectional view of the pipette tip shown in FIG. 5 taken along line A-A shown in FIG. 3.
Figure 6:
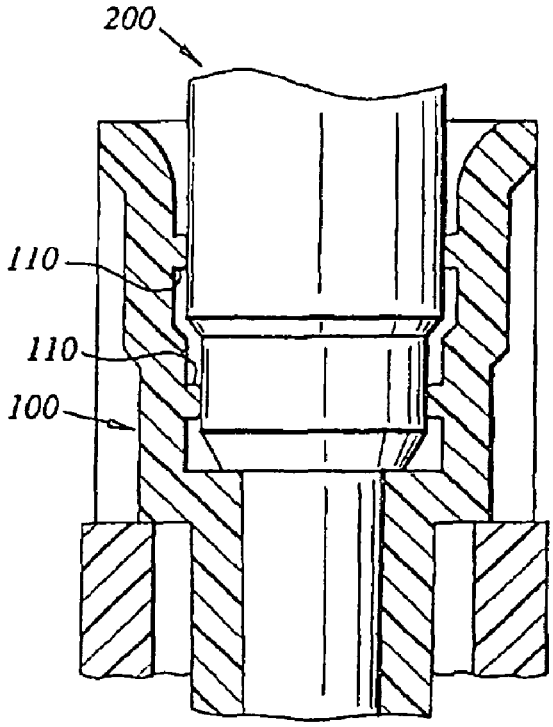
Fig. 6 Prior Art
FIG. 6 is a cross-sectional view of a prior art pipette tip with molded rings acting as seals on the pipette tip.

Another embodiment of the present invention further improves manufacturability of the pipette tips. In this embodiment, shown in FIGS. 3-5, the exterior of the collar portion 16 is defined by external ribs 17 that run parallel to the axis of the pipette tip. As shown in FIGS. 4 and 5, the external ribs 17 are positioned along a section of the collar portion 16 adjacent to the conical head portion 14 of the pipette tip 12. These ribs improve the flow of plastic into the tip during molding thereby improving the ease of manufacturing the tips. At the same time, by adding ribs, the wall of the collar portion 16, particularly the first step 24, may be made thinner. By thinning this wall, the forces required to insert or remove the mandrel 30 from the tip 12 are lowered because the wall of the collar portion 16 is easier to displace by the first band 40 on the mandrel during insertion or removal. As shown in FIG. 3, this embodiment also includes a molded internal ring 27 in the pipette tip 12 which is a positive stop for the mandrel 30 when it is inserted into the tip. This molded internal ring also functions as a "puller ring" that facilitates molding by keeping the tip on the core pin when the mold opens. Other puller rings 29 are included on the conical head 14 of the pipette tip 12. These puller rings 29 on the conical head 14 of the pipette tip 12 may also be included in other embodiments of the invention, such as that shown in FIG. 2A, to facilitate molding of the pipette tip.

The previously described versions of the present invention have many advantages including, but not limited to low insertion, sealing, and removal forces, and higher manufacturing yields for the custom molded pipette tips. Although the present invention has been described in considerable detail with reference to certain preferred versions thereof, other versions are possible. Therefore, the spirit and scope of the appended claims should not be limited to the description of the preferred versions contained herein.

What is claimed is:

1. A pipette mandrel for engagement with the interior wall of a pipette tip, the pipette mandrel comprising:

a. an elongated hollow structure, the hollow structure including a proximate end and a distal end;

b. a lead-in portion formed on the distal end of the hollow structure;

c. a first cylindrical portion adjacent to the lead-in portion, the first cylindrical portion having a first exterior diameter[.]*;* d. a second cylindrical portion adjacent to the first cylindrical portion, the second cylindrical portion having a second exterior diameter that is greater than the first exterior diameter;

e. a first non-resilient raised band positioned upon the first cylindrical portion, the first raised band having a diameter greater [that] *than* the first exterior diameter of the first cylindrical portion, the first raised band for contacting the interior wall of the pipette tip to form a first seal between the first raised band and the pipette tip; and f. a second raised band positioned upon the second cylindrical portion, the second raised band having a diameter greater [that] *than* the second exterior diameter of the second cylindrical portion, the second raised band for contacting the interior wall of the pipette tip to form a second seal between the second raised band and the pipette tip.

2. The pipette mandrel of claim 1 wherein the first raised band is adjacent to the lead-in portion such that the lead-in portion tapers into the first raised band.

3. The pipette mandrel of claim 1 further comprising a taper between the first and second cylindrical portion.

4. The pipette mandrel of claim 3, wherein the second raised band is positioned on the end of the second cylindrical portion substantially adjacent to the taper.

5. A pipette assembly comprising:

a. a pipette tip including a collar portion and an adjacent head, the head for receiving or expelling fluids from the tip, the collar portion including an interior cylindrical wall having a first interior diameter and a second interior diameter separated by a step portion, the interior cylindrical wall of the pipette tip further comprising a positive stop and the interior cylindrical wall void of any raised sealing rings; *and* b. a hollow mandrel having a proximate end and a distal end, the mandrel comprising:

(1) a lead-in portion formed on the distal end of the mandrel;

(2) a first cylindrical portion adjacent to the [lean-in] *lead-in* portion, the first cylindrical portion having a first exterior diameter;

(3) a first *non-resilient* raised band positioned upon the first cylindrical portion, the first raised band having a diameter greater [that] *than* the first exterior diameter of the first cylindrical portion, the first raised band contacting the interior cylindrical wall of the collar portion to form a first seal between the [mandrel and the pipette tip] *first non-resilient raised band and the interior cylindrical wall*; and (4) a second cylindrical portion adjacent to the first cylindrical portion, the second cylindrical portion having a second exterior diameter.

6. The pipette assembly of claim 5 wherein a flange between the collar portion and [conical] *the* head is the positive stop.

7. [The pipette assembly of claim 5] *A pipette assembly comprising:*

*a. a pipette tip including a collar portion and an adjacent head, the head for receiving or expelling fluids from the tip, the collar portion including an interior cylindrical wall having a first interior diameter and a second interior diameter separated by a step portion, the interior cylindrical wall of the pipette tip further comprising a positive stop,* wherein a puller ring on the interior wall of the pipette tip is the positive stop*, and the interior cylindrical wall void of any raised sealing rings; and*

*b. a hollow mandrel having a proximate end and a distal end, the mandrel comprising: (1) a lead-in portion formed on the distal end of the mandrel; (2) a first cylindrical portion adjacent to the lead-in portion, the first cylindrical portion having a first exterior diameter; (3) a first non-resilient raised band positioned upon the first cylindrical portion, the first raised band having a diameter greater than the first exterior diameter of the first cylindrical portion, the first raised band contacting the interior cylindrical wall of the collar portion to form a first seal between the mandrel and the pipette tip; and (4) a second cylindrical portion adjacent to the first cylindrical portion, the second cylindrical portion having a second exterior diameter.*

8. The pipette assembly of claim 7 wherein the collar portion of the pipette tip further comprises vertical ribs positioned on the exterior of the collar portion of the pipette tip.

9. The pipette assembly of claim 5 wherein the [mandrel further includes a second cylindrical portion adjacent to the first cylindrical portion, the second cylindrical portion having a second exterior diameter] *collar portion comprises a mouth comprising a funnel-shaped taper.*

10. The pipette assembly of [the] claim 9 wherein the mandrel further includes a second raised band positioned upon the second cylindrical portion, the second raised band having a diameter greater than the second exterior diameter of the second[:] cylindrical portion.

11. [The pipette assembly of claim 10] *A pipette assembly comprising:*

*a. a pipette tip including a collar portion and an adjacent head, the head for receiving or expelling fluids from the tip, the collar portion including an interior cylindrical wall having a first interior diameter and a second interior diameter separated by a step portion, the interior cylindrical wall of the pipette tip further comprising a positive stop and the interior cylindrical wall void of any raised sealing rings, wherein the collar portion comprises a mouth comprising a funnel -shaped taper; and*

*b. a hollow mandrel having a proximate end and a distal end, the mandrel comprising: (1) a lead-in portion formed on the distal end of the mandrel; (2) a first cylindrical portion adjacent to the lead-in portion, the first cylindrical portion having a first exterior diameter; (3) a first raised band positioned upon the first cylindrical portion, the first raised band having a diameter greater than the first exterior diameter of the first cylindrical portion, the first raised band contacting the interior cylindrical wall of the collar portion to form a first seal between the mandrel and the pipette tip; and (4) a second cylindrical portion adjacent to the first cylindrical portion, the second cylindrical portion having a second exterior diameter, wherein the mandrel further includes a second raised band positioned upon the second cylindrical portion, the second raised band having a diameter greater than the second exterior diameter of the second cylindrical portion,* wherein the second raised band contacts the interior cylindrical wall of the collar portion to form a second seal between the mandrel and the pipette tip.

12. A method for connecting a pipette mandrel to a pipette tip comprising:

a. providing a pipette tip comprising a collar portion and an adjacent conical head, the conical head for receiving or expelling fluids from the tip, the collar portion including an interior cylindrical wall having a first interior diameter;

b. providing a hollow mandrel having a proximate end and a distal end, the mandrel comprising:

(1) a lead-in portion formed on the distal end of the mandrel;

(2) a first cylindrical portion adjacent to the lead-in portion, the first cylindrical portion having a first exterior diameter, (3) a first non-resilient raised band [portioned] *positioned* upon the first cylindrical portion, the first raised band having a diameter greater than the first exterior diameter; [and]

(4) a second cylindrical portion having a second exterior diameter that is greater than the first exterior diameter; and (5) a second raised band positioned upon the second cylindrical portion, the second raised band having a diameter greater [that] *than* the second exterior diameter of the second cylindrical portion; *and* c. inserting said pipette tip onto said mandrel such that the first non-resilient raised band contacts the interior cylindrical wall of the collar portion to form a first seal between the mandrel and the pipette tip and the second raised band contacting the cylindrical wall of the collar portion to form a second seal between the mandrel and the pipette tip.

13. The method of claim 12 comprising the step of removing the pipette tip from the mandrel such that the first raised band disengages the interior cylindrical wall of the collar portion.

[14. A pipette tip and mandrel assembly comprising:

a. a mandrel comprising (1) a first cylindrical portion having a first exterior diameter, the first cylindrical portion having a first non-resilient raised band positioned upon the first cylindrical portion;

(2) a second cylindrical portion connected to the first cylindrical portion, the first cylindrical portion having a second exterior diameter different than the first exterior diameter; and b. a pipette tip positioned upon the mandrel, the pipette tip comprising (1) a head for receiving and expelling liquids;

(2) a collar connected to the head, the collar designed and adapted to fit over the first cylindrical portion and the second cylindrical portion of the mandrel, the collar comprising an interior cylindrical wall having a first interior diameter portion and a second interior diameter portion such that the diameter of the second interior diameter portion is different than the diameter of the first interior diameter portion; wherein the first interior diameter portion of the collar engages the first non-resilient raised band of the mandrel to form a first seal, and the second interior diameter portion of the collar fits over the second cylindrical portion of the mandrel.]

[15. The pipette and mandrel assembly of claim 14 wherein the mandrel further comprises a second non-resilient raised band positioned upon the second cylindrical portion.]

16. [The pipette and mandrel assembly of claim 15] *A pipette tip and mandrel assembly comprising:*

*a. a mandrel comprising (1) a first cylindrical portion having a first exterior diameter, the first cylindrical portion having a first non-resilient raised band positioned upon the first cylindrical portion; (2) a second cylindrical portion comprising a second non-resilient raised band positioned upon the second cylindrical portion connected to the first cylindrical portion, the first cylindrical portion having a second exterior diameter different than the first exterior diameter; and*

*b. a pipette tip positioned upon the mandrel, the pipette tip comprising (1) a head for receiving and expelling liquids; (2) a collar connected to the head, the collar designed and adapted to fit over the first cylindrical portion and the second cylindrical portion of the mandrel, the collar comprising an interior cylindrical wall having a first interior diameter portion and a second interior diameter portion such that the diameter of the second interior diameter portion is different than the diameter of the first interior diameter portion; wherein the first interior diameter portion of the collar engages the first non-resilient raised band of the mandrel to form a first seal, and the second interior diameter portion of the collar fits over the second cylindrical portion of the mandrel,* wherein the second interior diameter portion of the collar engages the second non-resilient raised band of the mandrel to form a second seal.

17. [The pipette and mandrel assembly of claim 14] *A pipette tip and mandrel assembly comprising:*

*a. a mandrel comprising (1) a first cylindrical portion having a first exterior diameter, the first cylindrical portion having a first non-resilient raised band positioned upon the first cylindrical portion; (2) a second cylindrical portion connected to the first cylindrical portion, the second cylindrical portion having a second exterior diameter different than the first exterior diameter; and*

*b. a pipette tip positioned upon the mandrel, the pipette tip comprising (1) a head for receiving and expelling liquids; (2) a collar connected to the head, the collar designed and adapted to fit over the first cylindrical portion and the second cylindrical portion of the mandrel, the collar comprising an interior cylindrical wall having a first interior diameter portion and a second interior diameter portion such that the diameter of the second interior diameter portion is different than the diameter of the first interior diameter portion; wherein the first interior diameter portion of the collar engages the first non-resilient raised band of the mandrel to form a first seal between the first non-resilient raised band of the mandrel and the first interior diameter portion of the collar, wherein the second interior diameter portion of the collar fits over the second cylindrical portion of the mandrel,* wherein the interior cylindrical wall of the pipette tip is void of any raised sealing rings.

[18. The pipette assembly of claim 14 wherein the interior cylindrical wall of the pipette tip further comprises a positive stop.]

*19. A pipette tip for use with a mandrel, the pipette tip comprising*

*a head for receiving and expelling liquids; and*

*a collar connected to the head and comprising a first internal cylindrical surface region that is divided by a molded internal ring, the molded internal ring serving as a positive stop for the mandrel when the mandrel is inserted into the pipette tip, wherein the diameter of the first cylindrical surface region is substantially the same on either side of the molded internal ring immediately adjacent to either side of the molded internal ring.*

*20. The pipette tip of claim 19 wherein the collar comprises a second internal cylindrical surface region such that the diameter of the second internal cylindrical surface region is different than the diameter of the first internal cylindrical surface region.*

*21. The pipette tip of claim 20 wherein the mandrel comprises a first cylindrical portion and a second cylindrical portion connected to the first cylindrical portion, wherein the first cylindrical portion comprises a first non-resilient raised band, and wherein the first interior diameter portion of the collar is adapted to engage the first non-resilient raised band of the mandrel to form a first seal, and the second interior diameter portion of the collar is adapted to fit over the second cylindrical portion of the mandrel.*

*22. The pipette tip of claim 21 wherein the first and second internal surface regions are void of any raised sealing rings.*

*23. The pipette tip of claim 20 further comprising a tapered portion between the first internal cylindrical surface region and the second internal cylindrical surface region.*

*24. The pipette tip of claim 22 wherein the head comprises a conical shape.*

*25. The pipette tip of claim 20 wherein the first and second internal surface regions are void of any raised sealing rings.*

*26. The pipette tip of claim 19 wherein the pipette tip comprises polypropylene.*

*27. The pipette tip of claim 19 wherein the collar comprises a mouth defined by a rim and a funnel-shaped taper.*

*28. The pipette tip of claim 19 wherein the head is conically shaped.*

*29. The pipette tip of claim 19 wherein the collar further comprises a plurality of axial ribs.*

*30. The pipette tip of claim 20 wherein the mandrel comprises a first sealing feature and a second sealing feature, wherein the first interior diameter portion of the collar is adapted to engage the first sealing feature of the mandrel to form a first seal, and the second interior portion of the collar is adapted to engage the second sealing feature of the mandrel to form a second seal.*

*31. A pipette tip for use with a mandrel, the pipette tip comprising*

*a head for receiving and expelling liquids, wherein the head further comprises a plurality of puller rings formed in an interior of the head; and*

*a collar connected to the head and comprising a molded internal ring, which serves as a positive stop for the mandrel when the mandrel is inserted into the pipette tip.*

*32. A pipette tip configured to engage a mandrel comprising a first cylindrical portion having a first exterior diameter, the first cylindrical portion having a first non-resilient raised band positioned upon the first cylindrical portion; and a second cylindrical portion connected to the first cylindrical portion, the second cylindrical portion having a second exterior diameter different than the first exterior diameter, wherein the pipette tip comprises:*

*a head for receiving and expelling liquids; and*

*a collar connected to the head, the collar designed and adapted to fit over the first cylindrical portion and the second cylindrical portion of the mandrel, the collar comprising an interior cylindrical wall having a first interior diameter portion and a second interior diameter portion such that the diameter of the second interior diameter portion is different than the diameter of the first interior diameter portion,*

*wherein the first interior diameter portion of the collar is configured to engage the first non-resilient raised band of the mandrel to form a first seal between the first interior diameter portion of the interior cylindrical wall of the collar and the first non-resilient raised band of the mandrel, and the second interior diameter portion of the collar is configured to fit over the second cylindrical portion of the mandrel, wherein the interior cylindrical wall of the pipette tip is void of any raised sealing rings.*

*33. The pipette tip of claim 32 wherein the interior cylindrical wall of the pipette tip further comprises a positive stop.*

*34. A pipette tip configured to engage a mandrel comprising a first cylindrical portion having a first exterior diameter, the first cylindrical portion having a first non-resilient raised band positioned upon the first cylindrical portion; and a second cylindrical portion connected to the first cylindrical portion, the second cylindrical portion having a second exterior diameter different than the first exterior diameter, wherein the pipette tip comprises:*

*a head for receiving and expelling liquids; and*

*a collar connected to the head, the collar designed and adapted to fit over the first cylindrical portion and the second cylindrical portion of the mandrel, the collar comprising an interior cylindrical wall having a first interior diameter portion and a second interior diameter portion such that the diameter of the second interior diameter portion is different than the diameter of the first interior diameter portion, wherein the interior cylindrical wall of the pipette tip is void of any raised sealing rings, wherein the interior cylindrical wall of the pipette tip further comprises a positive stop, wherein the positive stop is in the form of a molded internal ring,*

*wherein the first interior diameter portion of the collar is configured to engage the first non-resilient raised band of the mandrel to form a first seal, and the second interior diameter portion of the collar is configured to fit over the second cylindrical portion of the mandrel.*

*35. A method for connecting a pipette mandrel to a pipette tip, the pipette tip comprising a collar portion and an adjacent conical head, the conical head for receiving or expelling fluids from the tip, the collar portion including an interior cylindrical wall having a first interior diameter, and the mandrel having a proximate end and a distal end, the mandrel comprising: (1) a lead-in portion formed on the distal end of the mandrel; (2) a first cylindrical portion adjacent to the lead-in portion, the first cylindrical portion having a first exterior diameter, (3) a first non-resilient raised band positioned upon the first cylindrical portion, the first raised band having a diameter greater than the first exterior diameter; and (4) a second cylindrical portion having a second exterior diameter that is greater than the first exterior diameter; and (5) a second raised band positioned upon the second cylindrical portion, the second raised band having a diameter greater that the second exterior diameter of the second cylindrical portion, the method comprising:*

*inserting said pipette tip onto said mandrel such that the first non-resilient raised band contacts the interior cylindrical wall of the collar portion to form a first seal between the mandrel and the pipette tip and the second raised band contacting the cylindrical wall of the collar portion to form a second seal between the mandrel and the pipette tip.*

*36. The method of claim 35 further comprising the step of removing the pipette tip from the mandrel such that the first raised band disengages the interior cylindrical wall of the collar portion.*

* * * * *